(12) United States Patent
Lang

(10) Patent No.: US 7,862,774 B2
(45) Date of Patent: Jan. 4, 2011

(54) ANALYZER SYSTEM AND DRIVE MECHANISM FOR SAME

(75) Inventor: Karl Lang, Jona (CH)

(73) Assignee: Mettler-Toledo AG, Greifensee (CH)

( * ) Notice: Subject to any disclaimer, the term of this patent is extended or adjusted under 35 U.S.C. 154(b) by 2023 days.

(21) Appl. No.: 09/765,112

(22) Filed: Jan. 18, 2001

(65) Prior Publication Data

US 2001/0021354 A1 Sep. 13, 2001

(30) Foreign Application Priority Data

Jan. 19, 2000 (DE) ................................ 100 01 895

(51) Int. Cl.
*G01N 35/10* (2006.01)
*B08B 3/02* (2006.01)
*B08B 3/04* (2006.01)

(52) U.S. Cl. ........................ 422/81; 422/50; 73/864.22; 73/864.24; 134/21; 134/22.11; 134/22.12; 134/170; 134/64 R

(58) Field of Classification Search ................. 134/198; 436/49

See application file for complete search history.

(56) References Cited

U.S. PATENT DOCUMENTS 3,266,322 A * 8/1966 Negersmith et al. ...... 73/864.22
3,552,212 A    1/1971 Öhlin ....................... 73/864.22
4,338,280 A * 7/1982 Ambers et al. ............. 422/68.1
5,650,122 A * 7/1997 Harris et al. .................. 422/81
5,935,537 A * 8/1999 Schad ......................... 422/300
6,003,531 A * 12/1999 Kimura et al. .............. 134/198
6,422,248 B1 * 7/2002 Furst et al. ............... 134/22.11
7,325,555 B2 * 2/2008 Caderas ..................... 134/64 R
2001/0031223 A1 * 10/2001 Lang et al. ..................... 422/64

FOREIGN PATENT DOCUMENTS

| AT | 354162 | 12/1979 |
| DE | 3405234 | 8/1985 |
| DE | 3405962 | 8/1985 |
| DE | 3839896 | 6/1989 |
| WO | 9735173 | 9/1997 |

\* cited by examiner

*Primary Examiner*—P. Kathryn Wright
(74) *Attorney, Agent, or Firm*—Standley Law Group LLP

(57) ABSTRACT

An analyzer system has an instrument holder that can hold at least two instruments and is movable along a vertical guide. At least one washing device is provided for the instruments, with one or more jet orifices fed by a supply conduit to spray wash fluid at the instruments. The washing device comprises one or more wash rings surrounding the instruments. The washing device is separate from and movable in relation to the instrument holder, and the one or more jet orifices are aimed at the instruments positioned inside the one or more wash rings.

32 Claims, 6 Drawing Sheets

ANALYZER SYSTEM AND DRIVE MECHANISM FOR SAME

BACKGROUND OF THE INVENTION

The invention relates to an analyzer system of a kind generally used for performing chemical titrations. A known analyzer system has a vertical guide on which an instrument holder is constrained to a limited range of vertical movement. The system includes one or more washing devices for at least two instruments that are positioned on the instrument holder. The washing device has at least one jet orifice that receives wash fluid by way of a supply conduit arrangement and serves to spray the fluid at the instruments to be washed. While analyzer systems of this type are known to be used for titrations, the invention is not limited to titrator systems, but is generally applicable to analyzer systems with at least one instrument or device that requires washing after an analysis has been performed. The devices or instruments to be washed include, in particular, devices of an elongated shape such as a slender tube for dispensing an additive or to aspirate a fluid sample. Elongated devices, in the present context, include devices which, by themselves are not of an elongated shape, but have an elongated carrier.

Analyzer systems of the type just described are commercially available in a variety of different designs. The washing device in one such system uses a revolving circle of jets, e.g., in the form of a centrally located Segner turbine that sprays jets of washing fluid towards the outside and thereby propels itself into rotation. With devices of this kind, several instruments or devices of a system can be sprayed with relatively high intensity and at different surface areas. However, it is hardly avoidable that washing fluid escapes from the instrument, causing the surrounding areas to become contaminated. Therefore, the washing process is always performed inside a measuring container that holds a sample fluid. Thus, with an instrument such as a measuring electrode being partially immersed in the sample fluid, only a portion of the instrument can be cleaned.

Likewise known among the existing state of the art are designs where the instrument holder itself has a plurality of receiving holes for elongated instruments of the aforementioned kind, and where each receiving hole is equipped with a wash-jet orifice. However, this concept does not allow different surface areas of the instrument to be sprayed. Rather, the wash fluid always reaches only a segment of the entire circumference of the instrument, from where the wash fluid runs downward. Thus, when pulling an elongated instrument out of its receiving hole on the instrument holder, the entire length will be exposed to the spray, but only over a limited angular portion of the circumference.

As is obvious in this latter case, wash fluid has to be supplied to each individual receiving hole. The supply conduits take up space between the holes, which reduces the number of receiving holes, and thus the number of instruments, that can be accommodated in a given limited area.

Object of the Invention

It is therefore the objective of the present invention to further develop an analyzer system of the aforementioned kind, so that an effective washing operation can be performed without the risk of spraying washing fluid outside of the sample container.

SUMMARY OF THE INVENTION

According to the invention, the objective just stated is met by providing the analyzer system with a washing device in the form of at least one wash ring that is separate from and movable in relation to the instrument holder. The washing device surrounds the instruments held by the instrument holder and has at least one wash-jet orifice aimed at the instruments that are positioned inside the wash ring.

Because the instrument holder and the ring-shaped washing device are two separate parts, an intensive washing process can take place, comparable to the known solution with a Segner turbine. The washing device itself does not necessarily have to be a continuous ring extending over 360°, although this is preferred under the present invention. In any case, the concept of at least one jet orifice directed to the inside of a wash ring surrounding the instruments, i.e., a radially inward directed jet orifice, prevents wash fluid from being sprayed to the outside and thus eliminates the risk of undesirable contamination. Furthermore, the washing process can also take place outside of a sample container, with a higher intensity and possibly in less time than with existing state-of-the-art apparatus.

As mentioned above, the invention calls for the instrument holder and the ring-shaped washing device to be two separate parts. It is also within the scope of the invention that the instrument holder and the washing device could have separate guides to constrain them to a given range of movement relative to each other. However, it is preferred for the washing device to share the same vertical guide with the instrument holder, because this requires less space and simplifies the design.

It would also be conceivable to arrange the washing device in the same plane or even slightly above the level of the instrument holder, with wash-jet orifices slanted at a downward angle. However, in the preferred embodiment, the washing device is arranged below the instrument holder.

Similar to the know solution with a Segner turbine, one could provide a single wash-jet orifice that is driven to revolve around the at least one instrument seated in the instrument holder, e.g., with an inward-directed Segner turbine propelled by a more or less pronounced tangential component of the wash jet. However, regardless of whether the wash-jet orifice is movable or stationary, a more effective washing action is achieved if the wash ring has at least two wash-jet orifices distributed over its circumference. The orifices can be at substantially opposite locations of the circumference, or at equal angular intervals in the case of more than two orifices. As will be described later, the wash-jet orifices can also be distributed on two wash rings surrounding the instrument or group of instruments to be washed, with part of the jets covering one segment of the circumference, e.g., one half, and the other part of the jets covering the rest.

In order to obtain the most evenly distributed washing effect possible on all surface portions, it is advantageous if the jet orifices are spaced at angular intervals of at least 10° and less than 180°, but preferably 15° to 20°. Thus, the optimized solution calls for a considerable number of orifices at angular intervals of much less than 180°.

The main problem with the known design with one wash jet arranged in a receiving hole of the instrument holder is that the spray jet of wash fluid can essentially not spread out over a larger area and is therefore concentrated on a single spot on the circumference of the instrument from where the fluid runs downward in the axial direction of the instrument. This problem is solved by the present invention, in that the at least one wash jet of the wash ring is arranged at a radial distance that is greater than the combined cross-sectional envelope of the instruments in the instrument holder. Consequently, the one or more wash jets cover the instruments from a certain distance. This not only allows the fluid jet to cover a wider target area and thus have a better washing effect, but also allows a more forceful jet at a higher pressure without the risk of spraying or contaminating areas that are not intended to come into contact with the wash fluid. As a further means of avoiding the latter problem, the invention not only calls for the one or more jet orifices of the wash ring to be inward-directed but also to be aimed at a predetermined downward angle.

The wash jet orifices are subject to conflicting requirements. On the one hand, they should be as narrow as possible in order to apply a fine, distributed spray of fluid to the surface of the instrument. On the other hand, the narrower the aperture of the orifice, the greater is the risk that it will become clogged by calcium deposits or contamination. According to the invention, a minimum orifice diameter of 0.3 mm, preferably 0.5 mm, and optimally 0.5 to 0.8 mm was found to be the best compromise.

Regarding again the aforementioned difficulty with a state-of-the-art arrangement where the jet orifices are located in the receiving holes of the instrument holder, the main problem was that the supply conduits to the orifices take a certain amount of space, which cuts down on the number of receiving holes that can be provided in the instrument holder. In contrast, the arrangement according to the present invention allows a great number of receiving holes to be provided. It is advantageous if the wash ring has at least one distributor channel for the wash fluid that is connected to the supply device and runs along the perimeter of the wash ring. The distributor channel is preferably configured as a ring channel, especially if the wash ring extends over a closed 360° circle.

A distributor channel of this kind is particularly simple to produce if the channel cross-section is constant over the entire length. However, with a variable cross-section, it is possible to supply specifically desired amounts of pressure to the individual orifices. In particular, with a variable aperture of the distributor channel, the orifices at the end of the channel can receive the same level of pressure as the orifices at the beginning of the channel, i.e., in the vicinity of the inflow junction. Also in the interest of supplying adequate pressure to the orifices, it is preferred according to the invention, if the average cross-sectional aperture of the distributor channel is larger than the cross-section of the one or more jet orifices, preferably in a ratio of at least 5:1, but optimally in a range from 10:1 to 50:1.

The supply of wash fluid from a fluid reservoir can essentially be accomplished in any conceivable way. For example, the wash ring could have a radially protruding nipple or a short connector pipe where a supply hose could be attached. However, this could subject the apparatus to a lateral pulling force. Also, the previously described elongated instruments that are commonly used with this type of apparatus are generally supplied by conduits from vertically above, which helps to keep the hoses from becoming tangled up. It is therefore advantageous according to the invention, if the wash-fluid supply arrangement has a supply channel that runs at least in part substantially parallel to the direction of vertical movement of the instrument holder.

Within the scope of the invention, it would also be possible to have several holders for individual instruments on the same vertical guide mechanism, each with its own wash ring. However, in the preferred arrangement, the instrument holder has receiving locations for at least two instruments, with one wash ring surrounding them in common.

To automate the work with the analyzer apparatus, it is advantageous if the instrument holder is movable along a vertical guide by means of a drive motor. The wash ring could have a separate drive source, as it is more advantageous in principle, if the movements of the instrument holder and the wash ring are controlled separately. However, for the sake of a simpler design arrangement, it is better if the vertical movement of the wash ring is generated from the same drive source.

For example, one could use a motor operable in either sense of rotation, combined with free-wheeling clutches that are effective in opposite directions, so that when the motor runs in one direction, it would drive the instrument holder, and in the other direction it would drive the wash ring. However, with this arrangement, the two parts could only be moved one after the other, so that time would be lost in the process. To solve this problem, a further developed concept within the present invention provides that the instrument holder and the wash ring have limited mobility in relation to each other, constrained by at least one take-along element, which has proven to be a particularly simple concept for achieving an advantageous kind of relative mobility between the instrument holder and the wash ring.

It is self-evident in an analyzer system according to the present invention that a plurality of process steps have to be performed in a certain time sequence, such as putting the sample in place, lowering the at least one elongated instrument into the sample, performing the measurement, washing the instrument, removing the sample container, etc. A lockstep sequence of this kind can be stressful to the operator of the equipment, apart from being inefficient as a manual procedure, and it is therefore advantageous to automate the process. Consequently, the invention also covers a drive mechanism with at least one motor that is controlled by a programmed controller device.

In practice, a drive mechanism according to the invention would typically be controlled by a stored program that includes at least the following steps:

a) lowering the instrument holder and the wash ring to a desired level;

b) performing the measurement;

c) vertical movement of the at least one instrument held by the instrument holder in relation to the wash ring while simultaneously spraying wash fluid from the wash ring.

A computer or processor can be programmed to monitor and evaluate the measurement results in step b) and to issue a signal at the completion of step b), so that step c) will be initiated.

Further details of the invention will be discussed in the following description of the embodiments that are schematically represented in the drawings.

DESCRIPTION OF PREFERRED EMBODIMENTS

Figure 1:
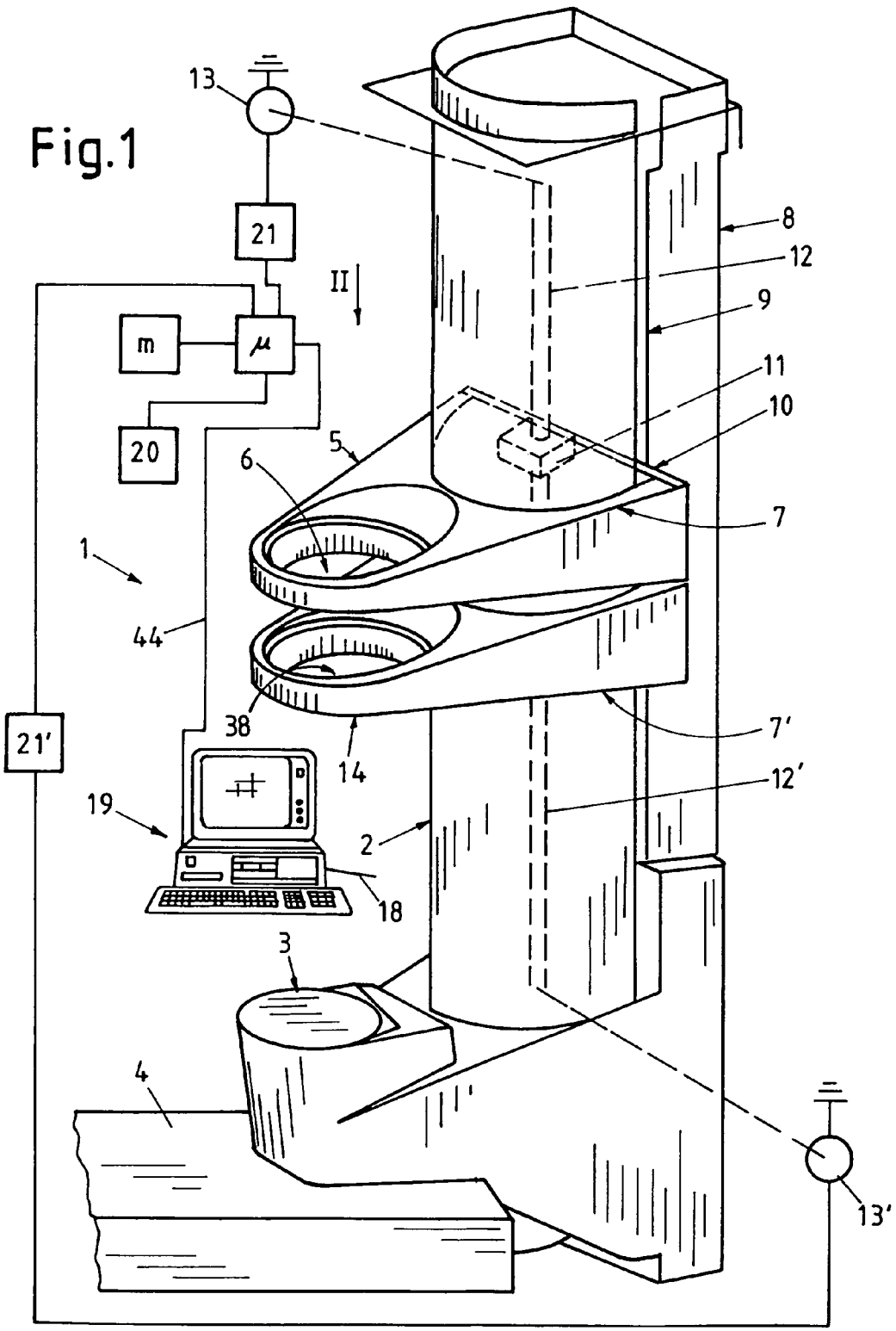
FIG. 1 represents a perspective view of a first embodiment of an analyzer system according to the invention, without any of the elongated instruments positioned in place.

FIG. 1 illustrates an analyzer system 1 with a vertical guide in the form of a guide column 2 located next to a sample support surface 3. At the bottom of the guide column 2, the system has a foot 4 of arbitrary design that gives stable support to the system and may also provide a surface on which to set down instruments and/or samples. The guide column 2 is held by a post 8 extending parallel to the guide column. The post 8 and the guide column 2 are separated by a vertical gap 9.

An instrument holder 5 is movable up or down along the vertical guide column 2. The instrument holder 5 has an opening 6 to receive a holder ring and a bracket portion 7. The bracket portion 7 embraces the vertical guide column 2 along a semi-circle. The bracket portion 7 has bracket arms with free ends reaching around both sides of the vertical guide column. The rearward-facing ends of the bracket arms are connected by a flat transverse brace 10. The transverse brace 10 is attached to the ends of the fork-like arms of the bracket 7, for example with screws.

As indicated by a broken line in FIG. 1, the transverse brace 10 is connected to at least one internally threaded block 11. The thread of the block 11 engages a spindle 12, rotatably mounted in bearings (not shown) inside the guide column 2 and extending, e.g., through half of the height of the guide column 2. The spindle 12 is driven by a motor 13, indicated only schematically in FIG. 1, with the possibility of using a reduction gear (not shown). The choice for the motor 13 is not limited per se. One could use, e.g., a direct-current motor, but a stepper motor is preferred. It goes without saying that many different solutions are possible for the design of the drive mechanism that is used to raise and lower the instrument holder 5 and a ring-shaped wash-jet holder 14 (see next paragraph), for example a vertical belt or chain drive, a linear motor, in particular a linear stepping motor, a ratchet feed, and other solutions.

Below the instrument holder 5, a separate wash ring 14 is likewise vertically movable along the guide column 2. The wash ring will be described farther below with reference to the preferred embodiment illustrated in FIGS. 3 and 4. In the embodiment of FIG. 1, the wash ring 14 is equipped with bracket arms 7' that are13 roughly speaking—analogous to the bracket arms 7 of the instrument holder 5. As will become evident later on, it is advantageous to provide an arrangement where the wash ring can move up and down independently of the instrument holder 5. Thus, one would not spontaneously expect the components 5 and 14 to share the same vertical guide column 2. Indeed, the wash ring could also have its own, separate vertical guide running parallel to the guide column 2. However, this could create problems in synchronizing the movements of the parts 5 and 14 in relation to each other and, in any event, it would require more space and could also obstruct the visibility of some system parts to the operator.

The wash ring 14 has a drive arrangement similar to the instrument holder 5, i.e., a spindle 12' that is driven by a motor 13'. However, as will be described in the following, it is possible to move the wash ring 14a (FIG. 2) up and down with only a single motor 13.

Figure 2:
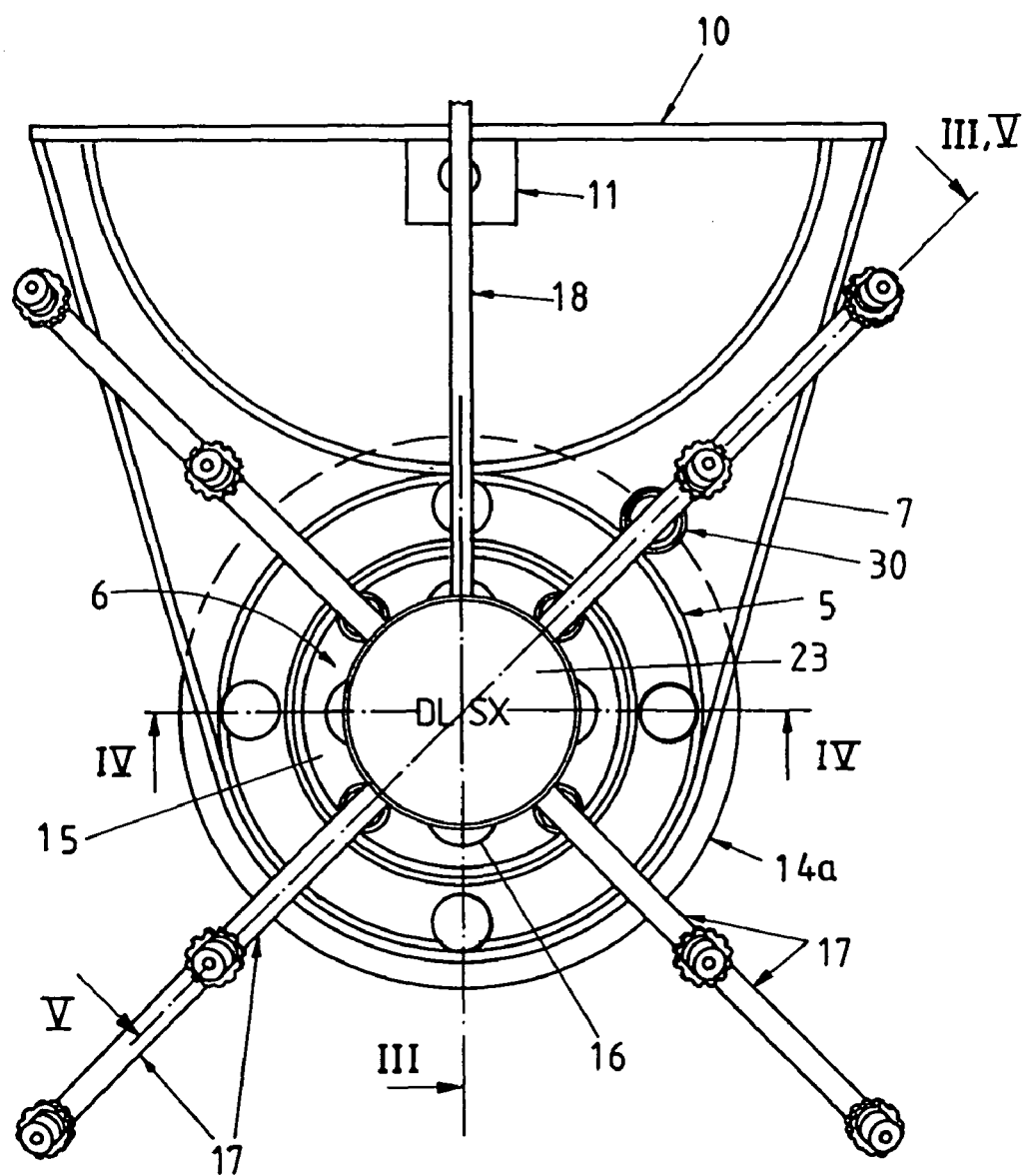
FIG. 2 represents a top view of the inventive analyzer system, as seen in the direction of the arrow II of FIG. 1, with instruments positioned in place.
Figure 3:
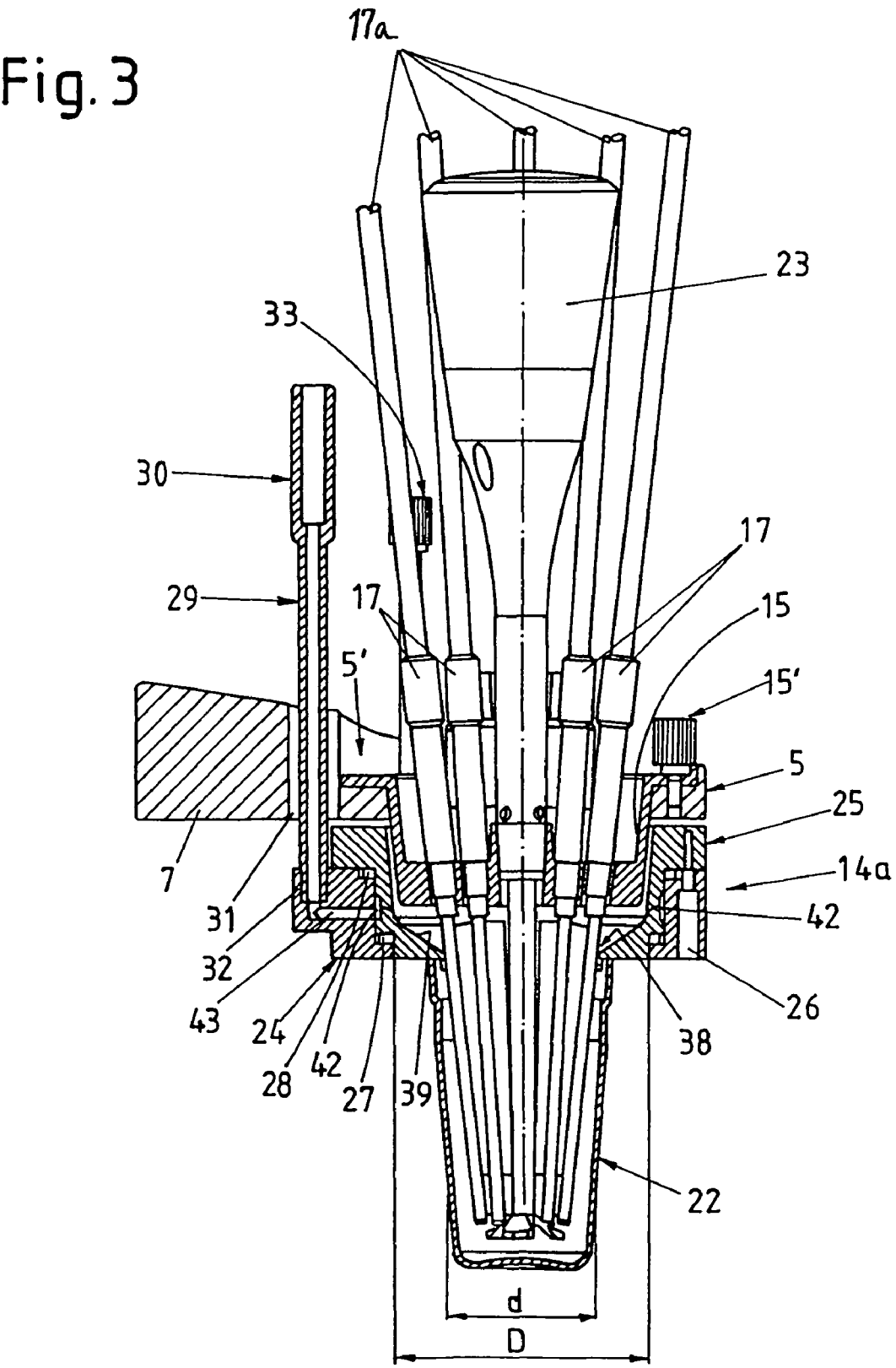
FIG. 3 represents a section along the line III-III of FIG. 2.
Figure 4:
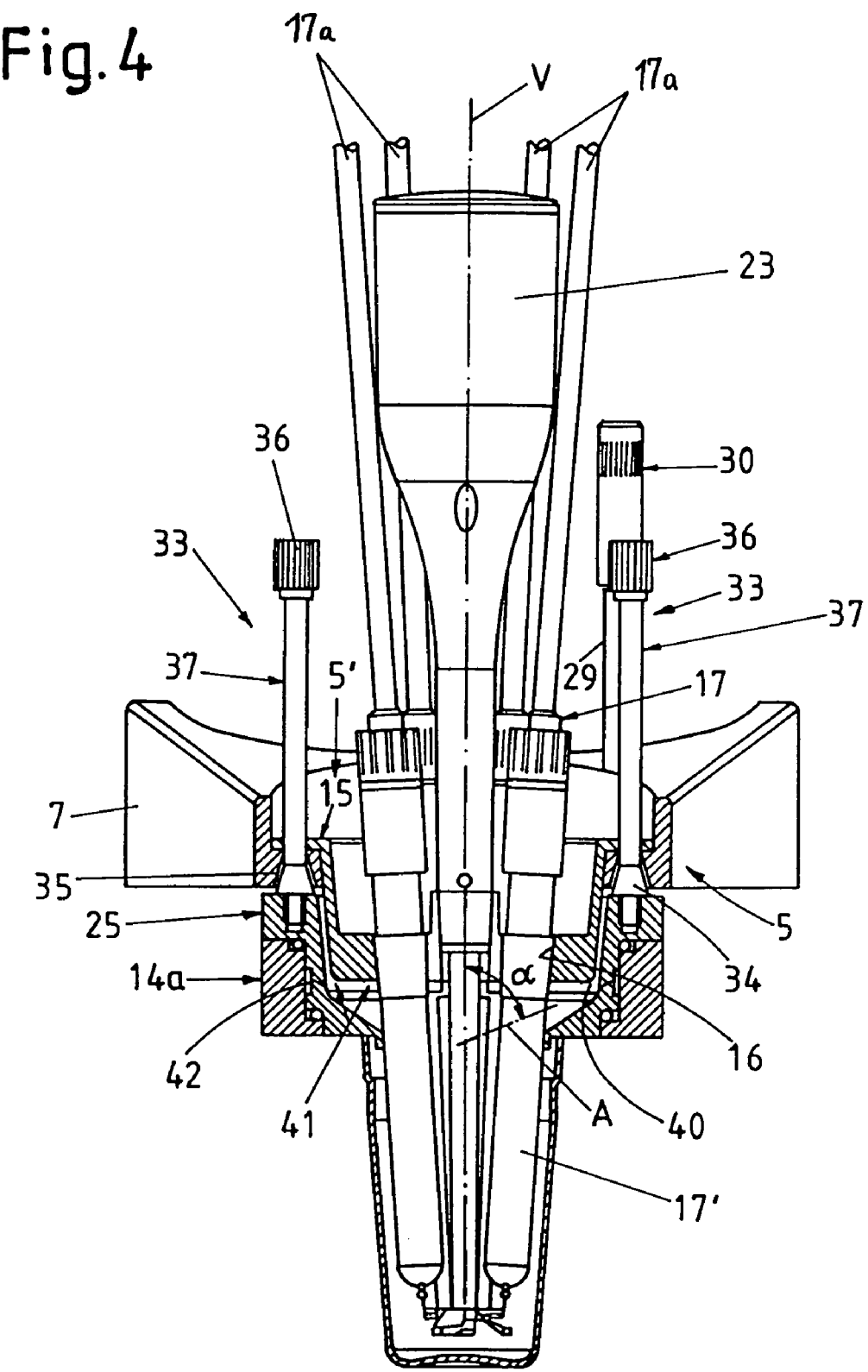
FIG. 4 represents a section along the line IV-IV of FIG. 2.

As illustrated in FIGS. 2, 3 and 4, the opening 6 of the instrument holder 5 is designed to receive a cup-shaped holder ring 15 with a knob handle 23 at the center. The holder ring 15 has receiving holes 16 for holding various elongated instruments such as, in the illustrated case, eight tubes 17, but the elongated instruments could also be pipettes or measuring electrodes. The holder ring 15 is held in place in a recess 5' by means of fastener screws 15' that are anchored in the rim portion surrounding the opening 6 of the instrument holder 5. As may be seen in FIG. 3, the cup-shaped holder ring 15 protrudes downward below the lower plane of the instrument holder 5. The measurement signals of the measuring electrodes 17 are sent to a computer 19 (FIG. 1) through at least one cable 18, which serves to collect and forward the signals of the individual electrode cables 17a (FIG. 3). It should be implicitly understood that the measuring electrodes or tubes 17 could also be held in place by other holder devices, although the use of a holder ring 15 has proved to be practical.

The aforementioned computer 19, which can in some cases cooperate with a microprocessor μ of the analyzer system, controls the time sequence of a measurement process that is programmed in a memory storage device m as described below. The process can be controlled in any number of different ways, e.g., by means of position sensors for the respective positions of the sample, the wash ring 14 and/or the instrument holder 5, but a time-dependent control by means of a clock generator 20 is preferred. The output signal of the microprocessor μ is sent to a control stage 21 for the motor 13 and to a control stage 21' for the motor 13' driving the spindle 12'. Also conceivable is a solution where the spindles 12, 12' are combined into a single spindle for controlling both of the aforementioned movements, with a right-hand thread in one part and a left-hand thread in another, using free-wheeling clutches that work in one direction in one section and in the opposite direction in the other section. Finally, it would also be feasible to use a single spindle that cooperates with selectively engageable counter-treads, e.g., a leaf spring that can be selectively engaged in or retracted from the spindle thread.

FIG. 3 illustrates an instrument holder 5 and a ring-shaped washing device 14 in a working position to perform measurements in a sample container 22 containing a liquid to be titrated. However, the invention is by no means limited to this application, although its primary use is in titration instruments. Another possible application is in the measurement of the moisture content of solids by means of probes, sensors or electrodes. Also possible is an application with a hardness-tester stylus, e.g., in a Vickers hardness tester.

The configuration of the wash ring 14a according to a preferred embodiment of the invention is illustrated with particular clarity in FIGS. 3 and 4. In contrast to the washing device or wash ring 14 of FIG. 1, the wash ring 14a of FIGS. 2 and 3 has no bracket arms 7'. Thus, the washing device 14a is configured to have only the ring portion without the bracket arms, with a connection to the instrument holder that allows the wash ring 14a to remain movable in relation to the instrument holder 5, as will be explained below. The wash ring 14a consists essentially of a supply channel ring 24 fastened to the underside of a wash-jet ring 25 by means of screws in screw holes 26 that are evenly distributed over the circumference of the rings 24 and 25. Interposed between the supply channel ring 24 and the wash-jet ring 25 are O-ring seals 27, 28.

The supply channel ring 24 is connected to a wash-fluid supply channel 29 that extends essentially parallel to the direction of the vertical up/down movement. The upper end portion 30 of the supply channel 29 has a larger diameter to allow a wash-fluid supply hose (not shown) to be connected. The supply channel 29 passes through a bore hole 31 of the instrument holder 5 in the area where one of the bracket arms 7 meats the main part of the holder 5 (FIG. 2). One could consider making the diameter of the bore hole 31 small enough that the widened head portion 30 of the supply channel 29 would serve as a take-along constraint for the wash ring 14a when the instrument holder is moving vertically. However, this is not an advantageous concept because for disassembly, it would necessitate pulling the supply channel 29 out of the supply-channel ring 24, where it is preferable for the supply channel 29 to remain sealed, as indicated by the sealing sleeve 32. Therefore, a design is favored where the diameter of the bore hole 31 is large enough to allow easy passage of the head portion 30 and to assign the take-along function to a separate part. A take-along constraint 33 provided for this purpose is indicated, but partially hidden, in FIG. 3 and may be seen more clearly in FIG. 4.

At least one take-along constraint 33, as shown in FIG. 4, is called for by the invention, but it is preferable to have several of the take-along bolts distributed at equal angles along the rings. The rod-shaped take-along bolts 33 have conical stops 34 and screw threads at their lower end portions, so that they can be screwed tightly into the wash-jet ring 25. The instrument holder 5 has conical holes 35 complementary to the stops 34, so that the stops 34 are seated in the holes 35 when the instrument holder is lowered into the position for performing a measurement. At their upper ends, the take-along bolts 33 have retainer heads 36. The latter could be integral with the bolt shafts, or they could be screwed onto the shaft section 37 at an adjustable position. Thus, the length of the shaft section 37 determines the range of relative mobility between the instrument holder 5 and the wash ring 14a, limited at the lower end by the conical centering stops 34 engaging the holes 35. At the other end of the range, when the retainer heads 36 seat themselves on the topside of the cup-shaped holder ring 15 resting in the opening 5', the wash ring 14a will be taken along if the instrument holder is raised further. Thus, a separate drive for the wash ring 14a becomes unnecessary. It goes without saying that the opening of the wash ring 14a can also be centered in other ways in relation to the opening 6 of the instrument holder 5. In particular, one could use separate centering pegs and -holes, but in view of the spatial constraints, it is especially advantageous to use the take-along bolts 33 to perform the centering function. With the arrangement described, a single motor 13 is sufficient to drive the up/down movement of both of the parts 5 and 14, so that the electrical components 13' and 21' as well as the bracket arms 7' and spindle 12' can be omitted. This benefits the simplicity of the construction of the analyzer system. The architecture of the apparatus is further simplified by the fact that the elongated instruments are surrounded by a common wash ring 14 or 14a, although it would be conceivable to use a separate wash ring for each instrument or for individual groups of instruments.

The wash-jet ring 25 that is bolted to the supply-channel ring 24 as shown in FIG. 3 has an opening 38 which, as a practical matter, is coaxial to the cup-shaped holder ring 15 so that, in the preferred embodiment, all instruments pass together through the same opening, although it would also be possible to have separate openings for the instruments as in the holder ring 15. However, this would make the apparatus more difficult to operate and would require more space. On the other hand, it is also possible to provide two or more wash rings, where one wash ring would have a common, large opening, while another wash ring would have several individual openings.

Above the passage opening 38, the wash ring 14a expands in an upward-widening cone section 39, which is followed by a steeper funnel section 40, as indicated in FIG. 4. The lower portion of the funnel section 40 has a ring of wash-jet orifices 41. The jet orifices 41 are at a certain distance from the measuring electrodes or tubes 17 traversing the passage hole 38, as illustrated in FIG. 3, and other measuring probes 17', as illustrated in FIG. 4, so that the jet streams emitted by the wash-jet orifices 41 can open up over the distance and spray a larger surface area of the instruments 17, 17' that are grouped together at the center. Accordingly, in the preferred embodiment, every wash-jet orifice 41 of the wash ring 14a is located on a circle of a diameter D that is greater than the diameter d of the opening 38 that surrounds the instruments. The larger diameter D, in comparison to d, also allows a greater number of wash jet orifices 41 to be accommodated. It is advantageous if the orifices 41 on the wash ring are spaced apart at angles of at least 10° and less than 180°, the preferred spacing being 15 to 20°. To ensure that the washing action covers all sides, it is in any case advantageous to use an arrangement with at least two jet orifices 41 in essentially opposite positions on the circle.

As may further be seen in FIG. 4, every wash jet 41 of the wash ring 14a is directed not only radially inward, but also at a predetermined downward angle $\alpha$ in relation to the vertical axis V (which is also the axis of the up/down movement). Preferably, the angle $\alpha$ is about 15° to 40°, with particular preference for a range from 20° to 30°. The downward angle of the spray jet has several advantages. For one, the distance to the instruments 17, 17' is increased, so that the spray jet can cover a wider area. In addition, the ring of jet orifices 41 can be arranged farther up in the wash-jet ring and thus at a greater diameter D, due to the conical internal shape of the wash ring. Thus, the ring of jet orifices 41 is raised high enough that the jet streams meet the instruments 17, 17' at a level where the latter would not even require washing. With the jet direction indicated by the dash-dotted line A in FIG. 4, the wash-fluid jets meet the surfaces of the instruments instrument 17, 17' only slightly below the receiving holes 16, so that the instrument parts that come into actual contact with the sample are entirely covered by the washing action. In addition, the slightly downward directed wash jets are more effective in dissolving and washing down any contaminating matter on the surface of the instruments.

As can be seen in the cross-sectional representation of FIGS. 3 and 4, the wash-jet orifices 41 lead from a distributor channel 42 to the internal funnel surface 40. As illustrated in FIG. 3, the distributor channel 42 is connected to the supply channel 29 by at least one (but preferably no more than one) transverse channel 43. The distributor channel 42 runs around the entire 360° of the wash-jet ring 25, i.e., the channel 42 is preferably a ring channel. Although it would be possible to split the distributor channel 42 into two branches of less than 180° originating from the junction with the transverse channel, it is not a preferred solution in view of manufacturing considerations. As explained above under "Summary of the Invention", the distributor channel 42 could along its course have a variable cross-sectional area, given that the orifice pressure will decrease more or less continuously from the junction with the transverse channel 43 to the orifices diametrically across from it, because of the amount of wash fluid exiting through the orifices along the way. However, this decrease in pressure is not of practical significance, and therefore it is sensible to design the distributor channel 42 with a constant cross-section over its entire length. Nevertheless, it is possible that one would want to achieve a higher pressure in some of the orifices 41 and that one would therefore design the distributor channel 42 with a variable cross-section; but in most practical applications, this would not be the preferred solution.

Likewise within the scope of the invention, it would be possible to arrange at least two rings of jet orifices 41, one above the other, whereby the orifices could be staggered and thus spaced closer together, with a separate channel 42 for each ring of orifices.

It is clear that the cross-sectional area of the channel 42 has to be relatively large in comparison to the cross-section of the wash-jet orifices 41, in order to supply a large number of orifices 41. It has been found that the average cross-sectional area of the distributor channel 42 needs to be large in comparison to the orifice cross-section even if there is only one jet orifice which may, for example, rotate around the vertical axis V. However, a wash-jet ring 25 that rotates in relation to the supply-channel ring 24 would require a more expensive solution for the seals than the simple O-rings 27, 28, and a drive source for the rotary motion would further add to the cost. Preferably, the ratio between the cross-sectional areas of the distributor channel 42 and the jet orifices 41 is at least 5:1, but with higher preference in a range from 10:1 to 50:1. For the reasons mentioned previously, it is advantageous if the wash-jet orifices 41 have a diameter of at least 0.3 mm, preferably 0.5 mm, with the highest preference for diameters from 0.5 to 0.8 mm.

Figure 5:
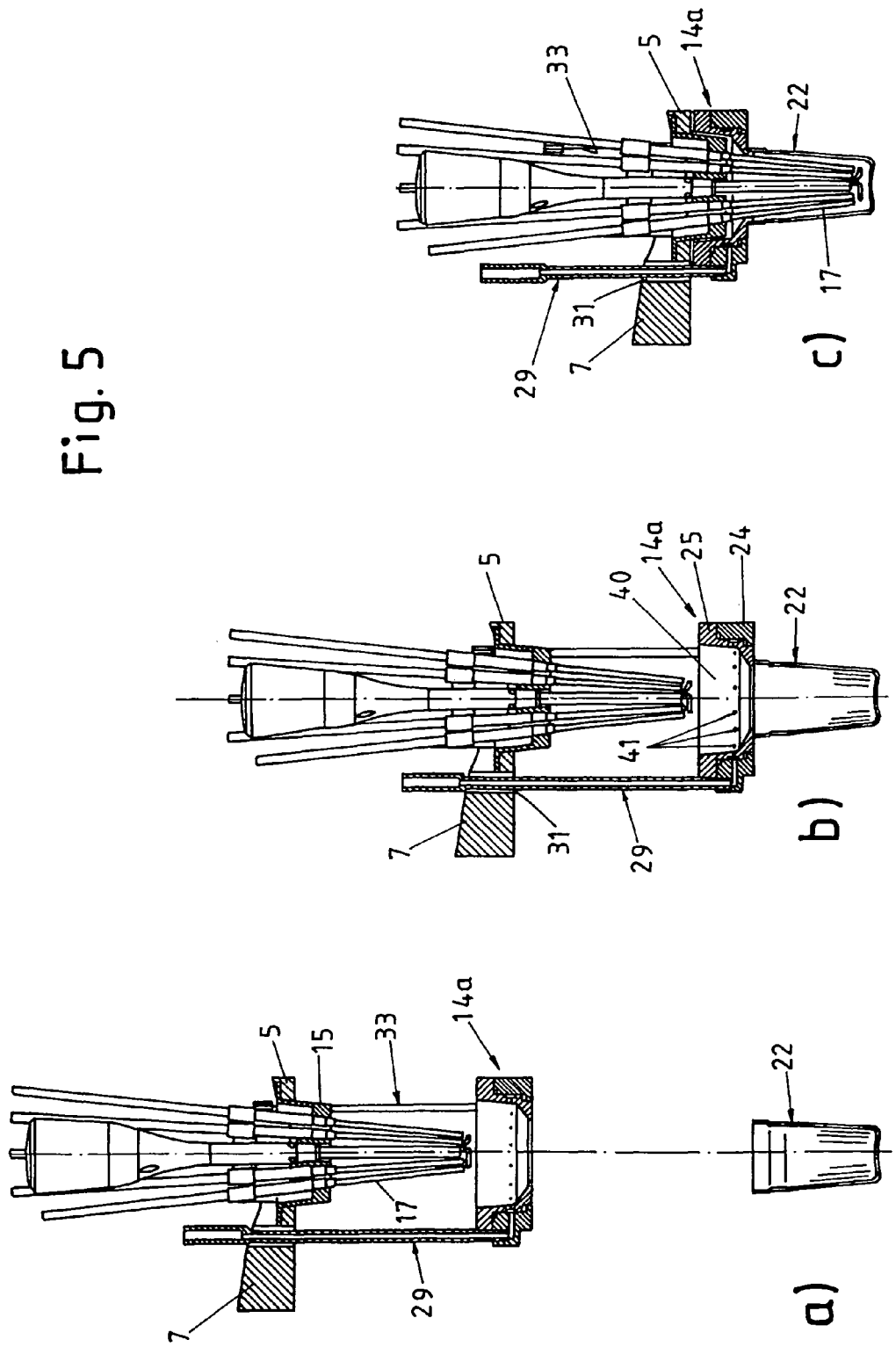
FIG. 5 shows the analyzer system at the principal stages a), b), c) of its program sequence, shown in a sectional view along the line V-V of FIG. 2.

As discussed previously, it is advantageous if the program memory m shown in FIG. 1 contains a stored program, the details of which will now be described in accordance with the program stages a) to c) of FIG. 5. The sequence of program stages shown in FIG. 5 and is based on the assumption that the analyzer system has only one drive motor 13, consistent with the embodiment of FIGS. 2 to 4. In principle, the washing process could be performed in a number of different ways, e.g., in the case of FIG. 1 by lowering the instrument holder into a sample and then raising it again. The wash ring 14 could also move upwards and deliver several spurts of spray as the instruments 17, 17' are moved up and down. However, the following procedure is preferred:

In the initial position shown in FIG. 5*a*, the instrument holder 5 with the measuring electrodes or tubes 17 seated in the holder ring 15 is at a position above the wash ring 14*a*, the latter being held at a set distance from the instrument holder 5 by the take-along bolts 33. The instrument holder 5 and the wash ring 14*a* are first lowered together to a level that is determined by the height of the sample container 22. This condition is shown in FIG. 5*b*. However, the desired target position for the instrument holder 5 is somewhat lower than the level where the wash ring 14*a* first settles on the rim of the container 22, which means that the instrument holder continues to move downward until the measuring electrodes 17 are immersed in the liquid test sample in the container 22. The end position is illustrated in FIG. 5*c*. The take-along bolts 33 have been pushed up through the holes above the conical openings 35, as illustrated in FIG. 4. The vertical supply channel 29, likewise moves upward in its passage opening 31 through the instrument holder 5.

At this stage, the measurement is performed. It is practical to initiate the process from the computer 19 (FIG. 1) by way of the signal acquisition cable 18 (FIGS. 1 and 2). After the measurement signals have been registered and evaluated by the computer, an "end of measurement" signal is given out by the computer. The "end of measurement" signal is transmitted through an output connection 44 to the microprocessor µ of the analyzer system, which monitors and controls the movements of the instrument holder 5 and wash ring 14*a*, whereas the computer 19 is dedicated exclusively to monitoring, performing and evaluating the measurements. It goes without saying that the processors 19 and µ could be parts of a single combined unit, where the microprocessor µ would be incorporated as a part of the computer 19.

Typically, the measurement is initiated by pressing a key or clicking on a screen icon on the computer 19. After the measurement has been completed, the parts 5 and 14*a* move in the reverse sense of FIG. 5, i.e., in the sequence c) to a). Due to the simplified design of the take-along bolts 33, the instrument holder 5 alone will be lifted up in a first phase of the movement, while the wash ring 14*a* remains seated on the rim of the container 22. The design of the wash-jet ring 25 with a relatively tall funnel surface 40 above the ring of jet orifices 41 proves to be advantageous, because it would prevent wash fluid from being sprayed to the outside even if the jet orifices 41 were not directed downward at an angle α.

During the upward movement of the instruments 17, 17' in relation to the wash ring 14*a*, the microprocessor µ under the direction of the program stored in the memory storage device m simultaneously releases the inflow of wash fluid from a wash-fluid reservoir (not shown) through a hose (likewise not shown) that is connected to the supply channel 29. Thus, in the course of their upward travel from position c) to b), the instruments 17, 17' are spray-washed from top to bottom, with the spent wash fluid dripping into the container 22. Subsequently, one could manually lift the wash ring 14*a* and remove the container 22. However, it is more practical if the instrument holder 5 and wash ring 14*a* are raised together from the position b) to a predetermined start position a), because the sample container 22 can be handled more conveniently if the space is clear.

As is self-evident from the foregoing description, the programmed sequence of the drive mechanism according to the invention could also be used to operate a Segner turbine of the existing state of the art, although the program and the drive mechanism are designed to work most advantageously with the analyzer system according to the invention.

Figure 6:
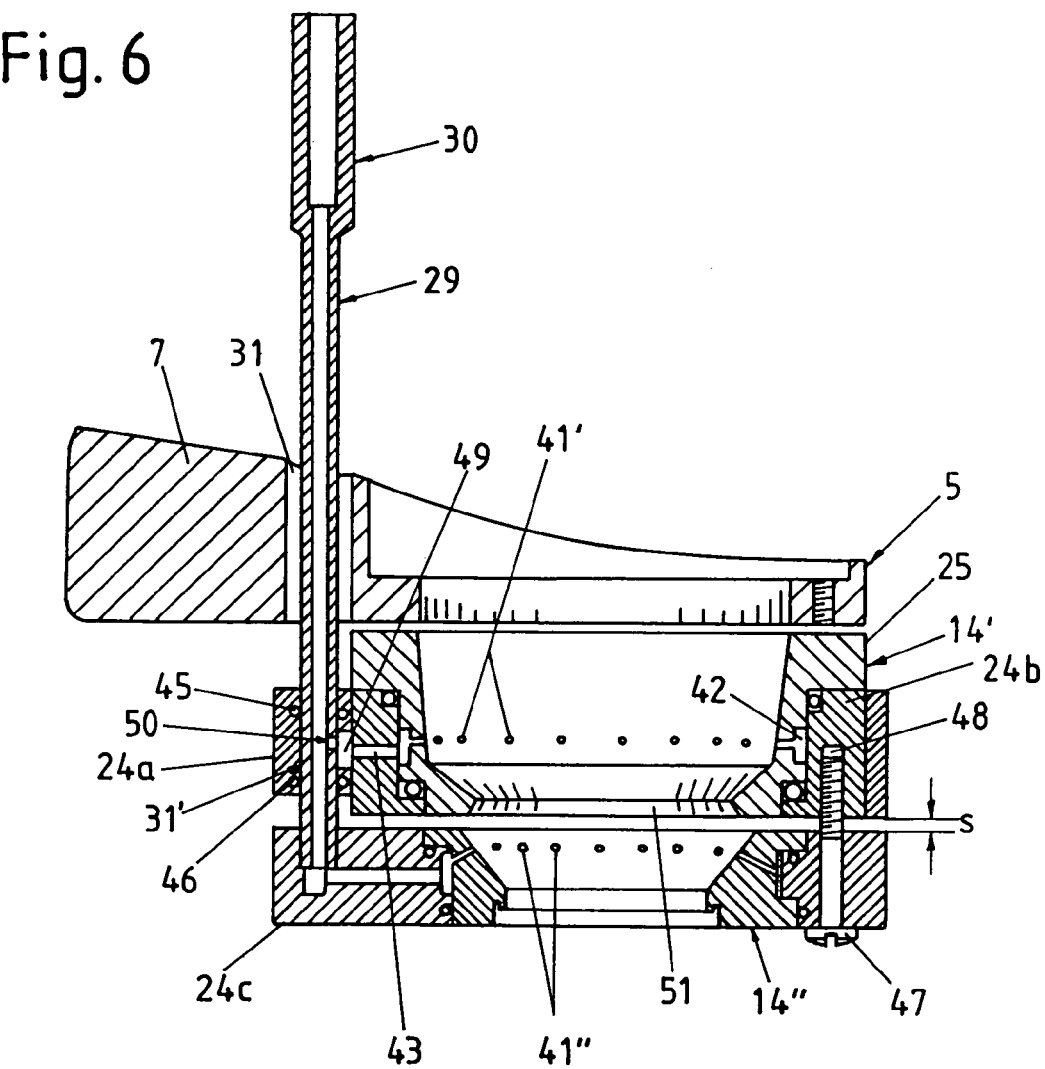
FIG. 6 represents a sectional view analogous to FIG. 3, but illustrating an embodiment where the washing device has two wash rings instead of one.

It can in some cases be desirable to provide a more intensive or otherwise modified washing arrangement for the instruments. This purpose can be accomplished with a design that has at least two wash rings 14', 14", as illustrated in FIG. 6. As in the example of FIG. 3, the supply channel 29 passes through the clearance opening 31 of the instrument holder 5. The supply channel also runs through a narrow bore 31' of an outer supply ring 24*a*, where the supply channel 29 is sealed against the bore hole 31', e.g., by two O-rings 45, 46. The bottom end of the supply channel 29 opens into the supply channel ring 24*c* of the further wash ring 14".

The wash rings 14', 14" are movable in relation to each other by a small amount s. The range s is predetermined by the length of one or more guide screws 47 which can be screwed into threaded holes 48 of an inner supply ring 24*b*, whereby a position adjustment between the wash rings 14', 14" is possible if desired. As may be seen in FIG. 6, the outer supply ring 24*a* is screwed onto the outside of the inner supply ring 24*b*. The seals 45, 46 can be configured to simultaneously seal the supply channel 29 and the interface between the rings 24*a*, 24*b*, but it is also possible to use separate seals.

Analogous to the arrangement of FIG. 3, the outer supply ring 24*a* has an axially extending chamber 49 from which a radial channel 43' leads to the jet orifices 41' by way of the distributor channel 42. The chamber 49 communicates with a radial outlet opening 50 of the supply channel 29 and is dimensioned so that within the adjustment range s between the wash rings 14', 14", the outlet opening 50 will always open into the chamber 49. The connection between the supply channel 29 and the lower wash ring 14", on the other hand, is accomplished in the same manner as in the embodiment of FIG. 3. Thus, both of the wash rings 14' and 14" are supplied with washing fluid by the same supply channel 29. As indicated in FIG. 6, the jet orifices 41" of the lower wash ring 14" of the illustrated embodiment are slanted upward, so that the fluid jets of the lines of orifices 41' and 41" are aimed approximately at the same target area when the wash rings 14' and 14" are set close together. To favor an unobstructed reach of the jet orifices 41" of the lower wash ring 14", the upper wash ring 14' has a downward-widening conical taper 51.

With a combination of wash rings 14', 14" of this kind, a variety of configurations are conceivable. For example, each wash ring could have its own supply channel 29, for example to allow different wash fluids to be dispensed from the two wash rings. Furthermore, the orifices 41' could be staggered in relation to the orifices 42". This allows the orifices to be arranged on a perimeter that is closer to the instruments. Of course, the wash jets of the orifices 41' and 41" do not have to be aimed in convergent directions. It is also possible to have both rows of jets pointed at a downward angle. Also, in certain cases an arrangement may be desired where the orifices 41' occupy only part of a circle, especially a semi-circle, while the rest of the circumference is covered by the orifices 41". It is further clear that, instead of a single ring of orifices 41 supplied by a distributor channel 42, each wash ring could have more than one row of orifices where, for example, an upper row of orifices could be aimed upward and a lower row of orifices could be aimed downward.

FIG. 6 also illustrates that the screws 47 work as take-along constraints, so that no separate drive mechanism is required for the wash rings 14', 14". However, separate drive mechanisms could be provided if desired, particularly in a case where the two wash rings are required to move in specifically controlled ways in relation to each other.

What is claimed is:

1. An analyzer system for immersing at least two instruments into a sample and removing the instruments therefrom, comprising:
   a vertical guide;
   an instrument holder constrained to move along the vertical guide to selectively immerse or remove the instruments, the instrument holder comprising a holder device with at least two apertures, each aperture arranged to receive and hold one of the at least two instruments;
   a washing device with a central opening, positioned between the instrument holder and the sample such that the central opening and the holder element are maintained in co-axial relationship as the at least two instruments pass through the central opening, the washing device comprising a jet orifice and a supply conduit for a wash fluid, communicated to the jet orifice.

2. The analyzer system of claim 1, wherein the washing device comprises a complete, closed wash ring surrounding the instruments over an angle of 360°.

3. The analyzer system of claim 2, wherein at least two jet orifices are distributed over an internal circumference of the wash ring.

4. The analyzer system of claim 3, wherein the jet orifices are disposed at substantially equal angular intervals.

5. The analyzer system of claim 3, wherein the jet orifices are disposed substantially at diametrically opposed locations.

6. The analyzer system of claim 3, wherein the jet orifices are disposed at angular intervals of at least 10° and less than 180°.

7. The analyzer system of claim 3, wherein the jet orifices are disposed at angular intervals of 15° to 20°.

8. The analyzer system of claim 1, wherein the washing device is constrained for guided movement along the vertical guide.

9. The analyzer system of claim 1, wherein the washing device is disposed vertically below the instrument holder.

10. The analyzer system of claim 1, wherein the jet orifice is disposed on a circumference of larger diameter than an internal opening width of the wash ring.

11. The analyzer system of claim 1, wherein the washing device has at least one wash ring with a common opening for all of the instruments.

12. The analyzer system of claim 1, wherein the orifice has a diameter of at least 0.3 mm.

13. The analyzer system of claim 12, wherein the orifice has a diameter of at least 0.5 mm.

14. The analyzer system of claim 13, wherein the orifice has a diameter of 0.3 to 0.8 mm.

15. The analyzer system of claim 1, wherein the jet orifice is aimed at a predetermined downward angle.

16. The analyzer system of claim 15, wherein the predetermined downward angle is substantially between 15° and 40°.

17. The analyzer system of claim 16, wherein the predetermined downward angle is substantially between 20° and 30°.

18. The analyzer system of claim 1, wherein:
   the instrument holder has an opening in which the holder device is removably seated.

19. The analyzer system of claim 1, wherein:
   the washing device is a wash ring and the jet orifice is aimed radially inward to the central opening to spray the wash fluid at a portion of the instruments passing through the central opening.

20. The analyzer system of claim 19, wherein the wash ring has a distributor channel for the wash fluid extending along a perimeter of said wash ring.

21. The analyzer system of claim 20, wherein the jet orifice has an orifice cross-section and the distributor channel has a channel cross-section that is larger than the orifice cross-section.

22. The analyzer system of claim 21, wherein the channel cross-section is at least five times as large as the orifice cross-section.

23. The analyzer system of claim 22, wherein the channel cross-section is ten to fifty times as large as the orifice cross-section.

24. The analyzer system of claim 1, wherein the washing device has at least two rows of jet orifices arranged one below the other.

25. The analyzer system of claim 24, wherein the rows of jet orifices are arranged on different wash rings.

26. The analyzer system of claim 25, wherein the washing device comprises wash rings that are movable in relation to each other.

27. The analyzer system of claim 25, further comprising a centering device interposed between the instrument holder and the washing device.

28. The analyzer system of claim 1, further comprising drive source that moves the instrument holder along the vertical guide.

29. The analyzer system of claim 28, wherein the drive source also moves the washing device along the vertical guide.

30. The analyzer system of claim 28, further comprising a take-along constraint allowing a limited range of relative movement between the instrument holder and the washing device.

31. The analyzer system of claim 1, wherein the supply conduit comprises a supply channel extending at least partially in parallel with the vertical guide.

32. The analyzer system of claim 1, wherein:

the washing device is separate from and movable in relation to the instrument holder.

\* \* \* \* \*

UNITED STATES PATENT AND TRADEMARK OFFICE
CERTIFICATE OF CORRECTION

| | | |
|---|---|---|
| PATENT NO. | : 7,862,774 B2 | Page 1 of 1 |
| APPLICATION NO. | : 09/765112 | |
| DATED | : January 4, 2011 | |
| INVENTOR(S) | : Lang | |

It is certified that error appears in the above-identified patent and that said Letters Patent is hereby corrected as shown below:

On the title page, Item (56) References Cited, please insert -- OTHER PUBLICATIONS
Patent Abstracts of Japan, JP 52-12893, Dainippon Tokyo K.K. --.

In column 5, line 53, please delete "are13 roughly" and insert -- are - roughly --.

Signed and Sealed this
Thirtieth Day of August, 2011

David J. Kappos
*Director of the United States Patent and Trademark Office*